(12) United States Patent
Cheng

(10) Patent No.: US 8,938,979 B2
(45) Date of Patent: *Jan. 27, 2015

(54) METHOD FOR LYOPHILIZATION USING CRYOGENIC REFRIGERATION SYSTEM

(75) Inventor: Alan Cheng, Naperville, IL (US)

(73) Assignee: Praxair Technology, Inc., Danbury, CT (US)

( * ) Notice: Subject to any disclaimer, the term of this patent is extended or adjusted under 35 U.S.C. 154(b) by 608 days.

This patent is subject to a terminal disclaimer.

(21) Appl. No.: 13/198,259

(22) Filed: Aug. 4, 2011

(65) Prior Publication Data

US 2011/0283717 A1     Nov. 24, 2011

Related U.S. Application Data

(62) Division of application No. 11/897,448, filed on Aug. 30, 2007, now Pat. No. 8,015,841.

(60) Provisional application No. 60/843,053, filed on Sep. 8, 2006.

(51) Int. Cl.
| | | |
|---|---|---|
| *A01N 1/02* | (2006.01) | |
| *F25D 3/10* | (2006.01) | |
| *F25D 17/02* | (2006.01) | |
| *F26B 5/06* | (2006.01) | |

(52) U.S. Cl.
CPC ............... *A01N 1/02* (2013.01); *A01N 1/0252* (2013.01); *F25D 3/10* (2013.01); *F25D 17/02* (2013.01); *F25D 2400/02* (2013.01); *F26B 5/06* (2013.01)
USPC .............................................................. 62/62

(58) Field of Classification Search
CPC .......................... A01N 1/0252; F25D 2400/02
USPC .................... 62/616, 532, 541, 62; 34/92
See application file for complete search history.

(56) References Cited

U.S. PATENT DOCUMENTS

| | | | | |
|---|---|---|---|---|
| 3,656,240 A | * | 4/1972 | Van Dijk | ............................ 34/92 |
| 3,788,096 A | | 1/1974 | Brilloit | |
| 4,407,140 A | * | 10/1983 | Kobayashi | ...................... 62/268 |
| 5,398,426 A | | 3/1995 | Connor | |
| 5,456,084 A | | 10/1995 | Lee | |
| 5,519,946 A | | 5/1996 | Renzi | |
| 5,701,745 A | | 12/1997 | Cheng et al. | |
| 5,743,023 A | | 4/1998 | Fay et al. | |
| 5,937,656 A | | 8/1999 | Cheng et al. | |
| 6,220,048 B1 | * | 4/2001 | Finan et al. | ..................... 62/434 |
| 2007/0186437 A1 | | 8/2007 | Gasteyer et al. | |

FOREIGN PATENT DOCUMENTS

| | | |
|---|---|---|
| DE | 20008915 | 6/2001 |
| EP | 0546931 A1 | 6/1993 |
| EP | 0989376 A2 | 3/2000 |

* cited by examiner

*Primary Examiner* — Frantz Jules
*Assistant Examiner* — Emmanuel Duke
(74) *Attorney, Agent, or Firm* — Robert J. Hampsch

(57) ABSTRACT

A cryogenic refrigeration system for lyophilization is disclosed. The cryogenic refrigeration system includes a cryogenic heat exchanger system adapted for vaporizing a liquid cryogen and using the gaseous cryogen to cool heat transfer fluid and a heat transfer cooling circuit that cools the lyophilization chamber as well as the condenser. The disclosed heat transfer cooling circuit includes a primary recirculation loop adapted for cooling the lyophilization chamber with the heat transfer fluid, a secondary recirculation loop adapted for cooling a condenser with the heat transfer fluid, and one or more valves operatively coupling the cryogenic heat exchanger system, the primary recirculation loop, and the secondary recirculation loop.

5 Claims, 2 Drawing Sheets

METHOD FOR LYOPHILIZATION USING CRYOGENIC REFRIGERATION SYSTEM

CROSS REFERENCE TO RELATED APPLICATIONS

This application is a divisional application of U.S. patent application Ser. No. 11/897,448 filed Aug. 30, 2007 now U.S. Pat. No. 8,015,841 which claims priority to U.S. patent application Ser. No. 60/843,053 filed Sep. 8, 2006, the disclosures of which are incorporated by reference herein.

FIELD OF THE INVENTION

The present invention relates to methods of lyophilization using cryogenic refrigeration systems, and more particularly to a cryogenic refrigeration system adapted to cool both a lyophilization chamber and the condenser using a common heat exchanger and heat transfer fluids.

BACKGROUND OF THE INVENTION

Lyophilization or freeze-drying is a sublimation process that removes free water or other solvent in the form of ice. Freeze-drying is especially useful in the pharmaceutical, chemical and food industries to remove water or solvent from sensitive synthetic and biological products because it preserves their integrity and activity. The increasing use of lyophilization is driven by the escalating global demand for aseptic packaging, preservation of drugs, and the rise in the production of biologics, including protein-based therapeutics and vaccines.

During lyophilization, most of the solvent (e.g. water and/or an alcohol) is removed from a product after it is frozen and placed under vacuum. The process actually consists of three separate, but interdependent steps: freezing; primary drying (ice sublimation); and secondary drying (moisture desorption). During primary drying, 90% or more of the solvent changes directly from solid to vapor phase through sublimation without passing through a liquid phase. The remaining solvent is adsorbed on the product as moisture. Some of this solvent is subsequently desorbed during the secondary drying process to reach the desired product stability. As a result of the lyophilization process, the solvent content in the product is reduced to a low level that can no longer support biological growth or chemical reactions, while still preserving the activity and integrity of the freeze-dried product.

Freeze-drying has traditionally been carried out commercially using mechanical freezing or refrigeration systems. Although mechanical refrigeration systems may be used, it is disadvantageous to do so because very low temperatures are needed in order to cause the water vapor to freeze out in the condenser of the freeze-dryer. Operating temperatures below $-50°$ C. adversely impact the performance, efficiency and reliability of the mechanical refrigeration systems.

Recent advancements in the field of freeze-drying employ the use of cryogenic fluids and cryogenic heat exchangers rather than mechanical refrigeration systems to carry out the freeze-drying process. The low operating temperatures required in a lyophilization process have no adverse impact on cryogenic refrigeration systems driven by liquid nitrogen with a normal boiling point of about $-196°$ C. Cryogenic refrigeration systems for lyophilization applications are capable of providing the rapid and constant cool-down rates throughout the entire temperature range of interest. Prior art cryogenic cooling systems recover the stored cold from liquid nitrogen in specially engineered cryogenic heat exchangers where the liquid nitrogen and/or gas nitrogen will cool a heat transfer fluid which in turn cools the lyophilization chamber. Separately, the cryogenic will cool the condenser by direct expansion in the condenser coils or plates. Unfortunately, the direct use in the condenser of any refrigerant—regardless whether it is a typical hydrocarbon refrigerant or a cryogenic fluid—results in two-phase flow and uneven heat exchange inside and non-uniform ice formation on the outside of the condenser coils or plates. Also, the use of separate cooling techniques or systems for the lyophilization chamber and the condenser introduces additional complexity of the overall system, increases the system footprint and likely adds some additional costs to own and operate the system.

What is needed therefore is an advanced cryogenic refrigeration system that protects the formulations during lyophilization and that provides increased flexibility, more uniform cooling and is cost competitive with comparable mechanical refrigeration systems and overcome the disadvantages of prior cryogenic refrigeration systems.

SUMMARY OF THE INVENTION

The present invention may be characterized as a method for lyophilizing a product comprising the steps of: (i) placing the product in a lyophilization chamber; (ii) cooling a heat transfer fluid in a cryogenic heat exchanger to a first temperature; (iii) freezing the product in the lyophilization chamber by circulating the cooled heat transfer fluid at the first temperature via a three way control valve disposed downstream of the heat exchanger system to a primary recirculation loop and to the lyophilization chamber and wherein the heat transfer fluid exiting the lyophilization chamber is recycled back to the lyophilization chamber or returned to the cryogenic heat exchanger system; (iv) further cooling the heat transfer fluid in the cryogenic heat exchanger to a second temperature; (v) drying the product in the lyophilization chamber by circulating the cooled heat transfer fluid at the second temperature via the three way control valve to a secondary recirculation loop and a condenser or circulating the cooled heat transfer fluid at the second temperature to both the lyophilization chamber via the primary recirculation loop and the condenser via the secondary recirculation loop and wherein the heat transfer fluid exiting the condenser is returned to the cryogenic heat exchanger system; and (vi) selectively diverting a portion of the heat transfer fluid in the secondary recirculation loop upstream of the condenser to the primary recirculation loop upstream of the lyophilization chamber to mix with the heat transfer fluid in the primary recirculation loop and lower the temperature of the heat transfer fluid in the primary recirculation loop and the lyophilization chamber.

BRIEF DESCRIPTION OF THE DRAWINGS

The above and other aspects, features, and advantages of the present invention will be more apparent from the following, more detailed description thereof, presented in conjunction with the following drawings, wherein.

DETAILED DESCRIPTION

Figure 1:
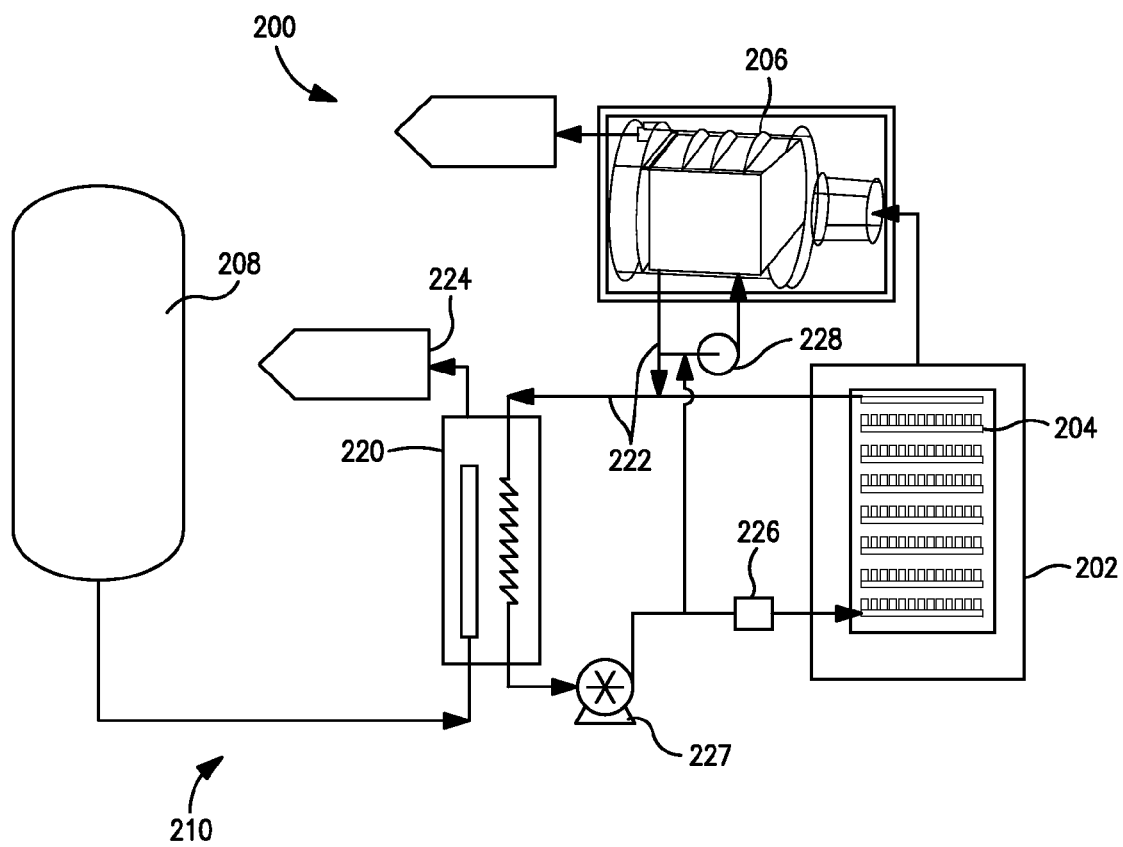
FIG. 1 is a high level schematic representation of a freeze dryer unit incorporating the present cryogenic refrigeration system.

With reference to FIG. 1, the illustrated freeze-dryer unit (200) has various main components plus additional auxiliary systems to carry out the lyophilization cycle. In particular, the freeze-dryer unit (200) includes a lyophilization chamber (202) that contains the shelves (204) and the formulation or product (not shown) to be lyophilized. The product to be lyophilized is specially formulated and typically contains the active ingredient, a solvent system and several stabilization agents. Lyophilization of this formulation takes place from specialized containers located on hollow shelves. These containers may include vials with stoppers, ampoules, syringes, or, in the case of bulk lyophilization, pans.

The illustrated freeze dryer unit (200) also includes a condenser (206) that is adapted to remove the sublimated and desorbed solvent from the vapor phase by condensing or freezing it out as ice to maintain adequate vacuum inside the freeze-dryer. The condenser (206) can be internally located in the lyophilization chamber (202) or as a separate external unit in communication with the lyophilization chamber (202) through a so-called isolation valve. The freeze dryer unit (200) also preferably includes a vacuum pump (208) operatively coupled to the condenser (206) and adapted to pull a vacuum on the lyophilization chamber (202) and condenser (206).

The cryogenic refrigeration system (210) provides the refrigeration for the freeze dryer unit (200) by cooling a prescribed heat transfer fluid which is circulated to the shelves (204) within the lyophilization chamber (202) and the condenser (206). As illustrated, the cryogenic refrigeration system (210) comprises a source of cryogen (208), such as liquid nitrogen, a cryogenic heat exchanger (220), and a heat transfer fluid circuit (222), a vent (224), a heater (226) and pumps (227,228).

The cryogenic heat exchanger (220) is preferably an NCOOL™ Non-Freezing Cryogenic Heat Exchange System available from Praxair, Inc. An important aspect of the cryogenic heat exchanger (220) is the vaporization of the liquid nitrogen within or internal to the heat exchanger yet in a manner that avoids direct contact of the liquid nitrogen on cooling surfaces exposed to the heat transfer fluid.

The prescribed heat transfer fluid circuit (222) is adapted to circulate a heat transfer fluid and is operatively coupled to both the lyophilization chamber (202) as well as the condenser (206). More specifically, the heat transfer fluid circulates inside the hollow shelves (204) within the lyophilization chamber (202) to precisely communicate the cooling or heating through the shelves (204) to the product as needed. In addition the prescribed heat transfer fluid also flows through the condenser (206) to provide the cooling means necessary to condense out the solvent vapors originating from the sublimating ice and desorbing solvent.

Pump (227) and heater (226) are disposed along the heat transfer fluid circuit (222) upstream of the lyophilization chamber (202) and downstream of the cryogenic heat exchanger (220). The pump (227) is sized to move the heat transfer fluid through the heat transfer circuit (222) at the required flow rates. The heater (226) is preferably an electric heater adapted to provide supplemental heat to the heat transfer fluid and the lyophilization chamber (202) as may be required during the drying processes.

As seen in the embodiment represented in FIG. 1, the condenser (206) is also cooled by a recirculating low temperature heat transfer fluid. Refrigeration of the heat transfer fluid flowing through the condenser (206) is also provided by a cryogenic heat exchanger (220). The cryogenic heat exchanger (220) is capable of cooling heat transfer fluid continuously without freezing. During the drying phases, the cryogenic heat exchanger (220) is set or adapted to achieve the lowest temperature required for the condenser (206). As described above, the cryogenic heat exchanger (220) pre-evaporates liquid nitrogen into a cryogenic cold gas for heat transfer to the heat transfer fluid. Through pre-evaporation of the liquid nitrogen assures the liquid nitrogen avoids boiling off directly over a heat exchange surface where the heat transfer fluid is disposed on the other side. Such arrangement avoids freezing of the cryogenic heat exchanger (220) since liquid nitrogen boils at about −196 degrees Centigrade at atmospheric pressure.

Although not shown, the freeze-dryer unit (200) also includes various control hardware and software systems adapted to command and coordinate the various parts of the freeze-drying equipment, and carry out the pre-programmed lyophilization cycle. The various control hardware and software systems may also provide documentation, data logging, alarms, and system security capabilities as well.

In addition, auxiliary systems to the freeze-dryer unit (200) may include various subsystems to clean and sterilize the lyophilization chamber (202), auto-load and unload the product in the lyophilization chamber (202); and associated cryogenic system accessories such as refrigeration skids, liquid nitrogen tanks, phase separating system, piping, valves, sensors, etc.

An important feature of the illustrated embodiment is the utilization of a single indirect non-freezing cryogenic heat exchange system (210) to provide refrigeration to the freezing chamber and the condenser simultaneously at different temperatures as needed. In typical freeze-drying applications the lyophilization chamber (202) requires a large refrigeration demand (i.e. large drop in temperature to freeze the product within the lyophilization chamber representing a load with large heat capacity and significant latent heat of fusion) for a relatively short period of time while the condenser (206) typically requires a lower refrigeration demand but for a significantly longer duration or cooling time.

It is also important in lyophilization applications that the temperature of the frozen product in the lyophilization chamber (202) be precisely controlled and often kept steady without any adverse temperature spikes or variations within the lyophilization chamber (202) including, for example, temperature variations within the lyophilization chamber of greater than about 1 or 2 degrees Centigrade.

Figure 2:
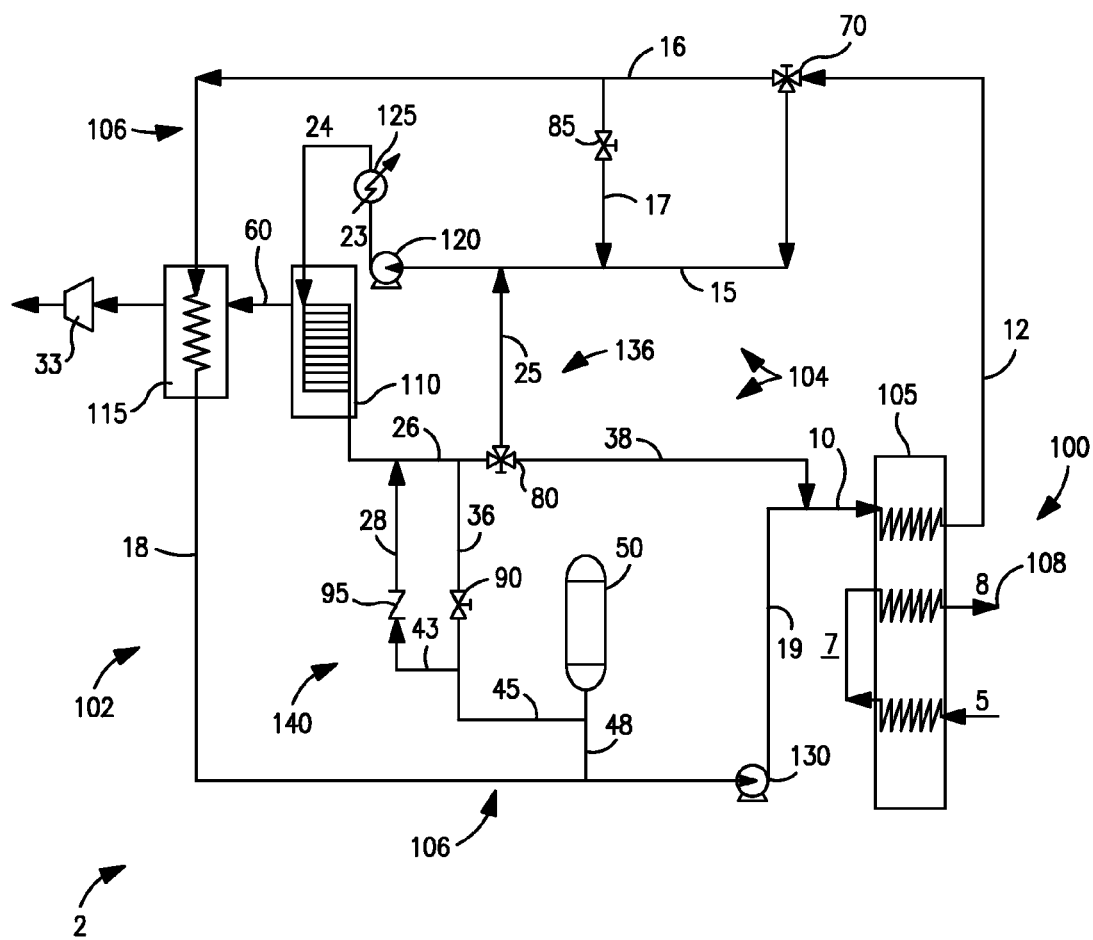
FIG. 2 is a more detailed schematic representation of the present cryogenic refrigeration system and the individual cooling circuits used in a lyophilization application.

Turning now to FIG. 2, there is shown another schematic representation of the preferred cryogenic refrigeration system (2) applied to or integrated within a freeze-dryer unit. In a broad sense the cryogenic refrigeration system (2) includes a cryogenic cooling circuit (100) and a flexible cooling circuit (102). In the illustrated embodiment, the heat transfer fluid flowing within the flexible cooling circuit (102) is controllably switched in and out of a primary recirculating loop (104) and a secondary recirculating loop (106) to effectively and efficiently satisfy the refrigeration loads and temperature requirements associated with both the condenser (115) and the lyophilization chamber (110).

The cryogenic cooling circuit includes a source of liquid nitrogen (not shown), a cryogenic heat exchanger (105), and an exhaust or vent line (108). Liquid nitrogen (5) at cryogenic temperatures is supplied to the cryogenic heat exchanger (105). Within the cryogenic heat exchanger (105), the liquid nitrogen (5) is vaporized into a cryogenic cold nitrogen gas (7). The cryogenic cold nitrogen gas (7) is redirected within the heat exchanger (105) to cool the incoming heat transfer fluid. After transferring most of its refrigeration capacity to the heat transfer fluid in the cryogenic heat exchanger (105), the residual nitrogen gas (8) is exhausted from the heat exchanger (105) via a vent line (108). In some applications, it may be possible to utilize the vented nitrogen gas in some other cooling application or industrial gas application within the facility. The structure and operation of the preferred cryogenic heat exchanger (105) is described in detail in U.S. Pat. No. 5,937,656 (Cheng et al.) the disclosure of which is incorporated by reference herein.

The heat transfer fluid flowing within the flexible cooling circuit (102) enters the cryogenic heat exchanger (105) via conduit (10), is cooled down by the vaporized cold nitrogen gas (7), and exits the cryogenic heat exchanger (105) via conduit (12) as a cold heat transfer fluid. The cold heat transfer fluid is circulated to the lyophilization chamber (110) via a primary recirculation loop (104) including a plurality of conduits (15, 23, 24, 26, and 38) and to the condenser (115) via a secondary recirculation loop (106) including a plurality of conduits (16, 18, and 19).

An important aspect of the illustrated embodiment is the flexible cooling circuit (102) that includes two recirculating loops (104,106) fed from the cryogenic heat exchanger (105) and fluidically coupled together by one or more cross-over valves (70, 80) and a diversion control valve (85). In this manner, the lyophilization chamber (110) may be cooled at the full refrigeration capacity (i.e. maximum cool-down rate) provided by the cryogenic heat exchanger (105) by directing substantially all or a significant portion of the cold heat transfer fluid exiting the cryogenic heat exchanger (105) directly to the lyophilization chamber (110) via the primary recirculation loop (104). Once the freezing of the product in the lyophilization chamber (110) is complete, the refrigeration demand for the lyophilization chamber (110) is reduced and the cold heat transfer fluid from the cryogenic heat exchanger (105) is redirected to the secondary recirculation loop (106) to meet the refrigeration demands of the condenser (115) during the primary and secondary drying phases of the lyophilization process.

Also, after the initial freezing phase and during the primary and secondary drying phases, the primary recirculation loop (104) is adapted to recirculate the heat transfer fluid through the lyophilization chamber (110) while restricting the return of the heat transfer fluid to the cryogenic heat exchanger (105). Thus, the primary recirculation loop (104) becomes a partially closed refrigeration loop adapted to keep the lyophilization chamber at the desired temperature.

Referring again to FIG. 2, during the primary and secondary drying phases the three-way valve (70) preferably redirects the cold heat transfer fluid from conduit (12) to the secondary recirculation loop and has completely stopped feeding the cold heat transfer fluid to the pump (120) of the primary recirculation loop (104). A second three-way valve (80) disposed in the primary recirculation loop (104) is also activated during the drying phases to redirect the heat transfer fluid in the primary recirculation loop (104) such that it no longer feeds the cryogenic heat exchanger (105). In this manner, an isolation circuit (136) is formed including conduits (23, 24, 25, and 26) with the heat transfer fluid exiting the lyophilization chamber (110) recirculating via conduits (25, 26) back to the pump (120) and again to the lyophilization chamber (110) via conduits (23, 24) and heater (125). To warm up the chamber (110) in a very slow and precise rate, a small amount of cold heat transfer fluid is bled from the secondary circuit (106) through the diversion control valve (85). This avoids over heating in the chamber (110) shelves for slow drying formulations.

As indicated above, the condenser (115) is cooled to the desired temperature by controlling the temperature and flow of heat transfer fluid in the secondary recirculating loop (106). During the primary and secondary drying phases, the flow of heat transfer fluid in the secondary recirculating loop (106) is generally fed from a stream of heat transfer fluid via conduit (12) directly from the cryogenic heat exchanger which is preferably at a desired temperature set point. However, a portion of the cold heat transfer fluid may be diverted via conduit (17) from the secondary recirculation loop (106) to the primary recirculation loop (104) to keep the primary recirculation loop (104) at the desired temperature when additional cooling is needed. In addition, a heater (125) is also used in the primary recirculation loop (104) and isolation circuit (136) to raise the temperature of the heat transfer fluid within the isolation circuit (136) and lyophilization chamber (110) when additional heating is needed. Such heating and cooling adjustments are preferably made at very slow, precise and controlled rates in order to maintain the temperatures of the shelves, vials and its contents at the desirable value.

Diversion of the cold heat transfer fluid from the secondary recirculation loop (106) to the primary recirculation loop (104) is preferably achieved using a diversion control valve (85) and a pump (120) operatively associated with the primary recirculation loop (104). The illustrated embodiment of FIG. 2 depicts a diversion loop (17) disposed between the primary recirculation loop (104) and the secondary recirculation loop (106). The diverted cold heat transfer fluid from the secondary recirculation loop (106) mixes with the warmer heat transfer fluid in the primary recirculation loop (104) that is isolated and recirculating through the lyophilization chamber (110).

Bleeding or diverting a small amount of heat transfer fluid from the secondary recirculation loop (106) to the primary recirculation loop (104) cannot occur if the primary recirculation loop (104) is fully closed and the line pressure in the secondary recirculation loop and in conduit (16) is lower or equal to the line pressure in the primary recirculation loop (104) and conduit (25). To make that transfer possible, pump (130) in the secondary recirculation loop (106) should have a higher flow capacity and pressure head than pump (120) in the primary recirculation loop (104). As the diverted cold heat transfer fluid flows into the primary recirculation loop (104), over pressurization may occurs. In such case, the excess flow is released by relief valve (90) into an overflow circuit (140) including a plurality of conduits (36, 43, 28, 45, and 48), valves (90, 95) and buffer tank (50).

The heat transfer fluid within the primary recirculation loop (104) will typically expand and contract during the drying phases as a result of the temperature swings caused by the continuous heating and cooling of the heat transfer fluid therein. To avoid cavitating the pumps, it is important that no gas bubbles be present in the recirculating loops from the heat transfer fluid expansion and contraction. To address this operating concern, the expanding heat transfer fluid is released from the primary recirculation loop via relief valve (90) as needed. Similarly, during the cooling temperature swings, the heat transfer fluid in the primary recirculation loop (104) will contract and a check valve (95) will open to allow backfill of the excess heat transfer fluid back into the primary recirculation loop (104). A buffer tank (50) is operatively disposed in the overflow circuit (140) to allow for the variations in volume due to the thermal expansion and contraction of the heat transfer fluid.

Operation of the embodiment illustrated in FIG. 2 is best understood from consideration of the following description. In a typical lyophilization process, the first operation is the freezing step where the shelves of the lyophilization chamber (110) are cooled down to a prescribed temperature. To facilitate the rapid cool-down of the lyophilization chamber (110), the cryogenic heat exchanger (105) is set to the desired lyophilization chamber temperature (e.g., −50 degree Centigrade). During this operation, a three-way valve (70) blocks the cold heat transfer fluid from going to the condenser (115) and diverts substantially all the fluid toward the lyophilization chamber (110) via conduit (15). A recirculating pump (120) moves this heat transfer fluid through the primary recirculation loop (104). In a typical application, the cold heat transfer fluid flowing through the primary recirculation loop (104) will reduce the temperature on the shelves to the desired temperature within 1 to 2 hours or less.

During this maximum cool-down rate phase or freezing phase, the heat transfer fluid exiting the lyophilization chamber (110) via conduit (26) may be a few degrees warmer than the heat transfer fluid in conduit (24) at the inlet of the lyophilization chamber (110). The warmer heat transfer fluid returns to the cryogenic heat exchanger (105) via a three-way transfer valve (80) adapted to controllably couple the heat exchanger with the primary recirculation loop (104). The warmer heat transfer fluid exits from the three-way valve (80) via conduit (38) and connects to the inlet line (10) of the cryogenic heat exchanger to form a complete heat transfer circuit for the lyophilization chamber (110).

During this freezing phase, the cryogenic refrigeration system (2) holds the temperature of the lyophilization chamber (110) at the prescribed set point for several hours to ensure the products inside the vials or pans placed on the shelves are frozen completely. The exact temperature profile during this freezing phase may vary depending on the product to be frozen. For example, some lyophilization processes require steep ramp down to the prescribed temperature, whereas other lyophilization processes require initial cool-down followed by a plateau or a late temperature rise in the lyophilization chamber to anneal the ice crystal structure in the product.

After the vials in the lyophilization chamber (110) have been properly chilled and the products are frozen, the second step is to chill the condenser (115) to start the primary and secondary drying processes. The condenser (115) must be cold enough to freeze and capture the water (or solvent) vapor leaving from the lyophilization chamber (110) via flow path (60) during the sublimation step. This is accomplished by changing the set point of the cryogenic heat exchanger (105) to be 10 to 20 degrees Centigrade colder than the lyophilization chamber temperature or about, −60 or −70 degrees Centigrade.

The three-way valve (70) is again activated to redirect the flow (15) from the cryogenic heat exchanger (105) to the condenser (115) via the secondary recirculation loop (106). The colder heat transfer fluid (e.g. at −60 degrees Centigrade) enters the condenser (115) and drops down the temperature of the condenser (115) at a prescribed rate. The warmer heat transfer fluid exiting the condenser (115) via conduit (18) may be a few degrees warmer than the temperature of the heat transfer fluid entering the condenser (115) via conduit (16). The warmer heat transfer fluid is then transferred back to the cryogenic heat exchanger (105) using a recirculating pump (130). The warmer heat transfer fluid exiting the pump (130) via conduit (19) returns to the cryogenic heat exchanger (105) through inlet line (10).

However, because the lyophilization chamber (110) needs to maintain a maximum uniform temperature at the shelves (e.g., −50 degrees Centigrade), a continuous flow of heat transfer fluid must be maintained in the isolated primary recirculation loop (104). Preferably, the temperature of the lyophilization chamber (110) should rise under a tight temperature control of not more than about 0.5-2.0 degrees Centigrade per hour. Temperature control of the lyophilization chamber (110) during this phase is preferably accomplished by bleeding in a small amount of the colder heat transfer fluid from the secondary recirculation loop (106) through diversion control valve (85) and diversion loop (17) where additional cooling of the heat transfer fluid is needed and/or heating the fluid within the primary recirculation loop with an electric heater (125) where additional heating of the heat transfer fluid is desired.

When the condenser (115) is fully cooled to its final temperature, vacuum is created by a vacuum pump (33) for both the condenser (115) and the lyophilization chamber (110). The ice in the frozen vials is being sublimated into water or solvent vapor under vacuum conditions and enters the colder condenser via flow path (60). The extracted water or solvent vapor is refrozen and condensed on the condenser surface as ice, and any non-condensable matter is passed to the vent. The condenser temperature setting is adjusted as needed to maintain the desired vacuum level in the lyophilization chamber.

While the present invention has been described with reference to a preferred embodiment, as will occur to those skilled in the art, numerous changes, additions and omissions may be made without departing from the spirit and scope of the present invention, as defined by the appended claims.

What is claimed is:

1. A method for lyophilizing a product comprising the steps of:
   placing the product in a lyophilization chamber;
   vaporizing a liquid cryogen and cooling a heat transfer fluid in a cryogenic heat exchanger to a first temperature using the gaseous cryogen;
   freezing the product in the lyophilization chamber by circulating the cooled heat transfer fluid at the first temperature via a three way control valve disposed downstream of the cryogenic heat exchanger to a primary recirculation loop configured to cool the lyophilization chamber and wherein the heat transfer fluid exiting the lyophilization chamber is recycled back to the lyophilization chamber or returned to the cryogenic heat exchanger;
   further cooling the heat transfer fluid in the cryogenic heat exchanger to a second temperature;
   drying the product in the lyophilization chamber by circulating the further cooled heat transfer fluid at the second temperature via the three way control valve to a secondary recirculation loop configured to cool a condenser or circulating the further cooled heat transfer fluid at the second temperature to both the lyophilization chamber via the primary recirculation loop and the condenser via the secondary recirculation loop and wherein the heat transfer fluid exiting the condenser is returned to the cryogenic heat exchanger; and
   selectively diverting a portion of the heat transfer fluid in the secondary recirculation loop via a diversion valve from a location downstream of the three way control valve and upstream of the condenser to the primary recirculation loop at a location downstream of the three way control valve and upstream of the lyophilization chamber to mix with the heat transfer fluid in the primary recirculation loop and lower the temperature of the heat transfer fluid in the primary recirculation loop and the lyophilization chamber.

2. The method of claim 1 wherein the temperature of the heat transfer fluid within the primary recirculation loop and the temperature of the lyophilization chamber are precisely controlled during the drying step by selectively: (i) heating the heat transfer fluid within the primary recirculation loop using a heater disposed in the primary recirculating loop to raise the temperature of the heat transfer fluid in the primary recirculation loop; and/or (ii) diverting a portion of the heat transfer fluid in the secondary recirculation loop to mix with the heat transfer fluid in the primary recirculation loop and lower the temperature of the heat transfer fluid in the primary recirculation loop and the lyophilization chamber.

3. The method of claim 1 wherein the heat transfer fluid exiting the lyophilization chamber is recycled back to the lyophilization chamber during the drying step without passing to the cryogenic heat exchanger.

4. The method of claim 1 wherein the heat transfer fluid exiting the lyophilization chamber is returned to the cryogenic heat exchanger during the freezing step.

5. The method of claim 1 wherein a portion of the heat transfer fluid in the primary recirculation loop is directed to an expansion circuit during volumetric expansion of the heat transfer fluid in the primary recirculation loop and heat transfer fluid from the expansion circuit is directed to the primary recirculation loop during volumetric contraction of the heat transfer fluid in the primary recirculation loop.

* * * * *